United States Patent [19]
Oka

[11] Patent Number: 5,797,838
[45] Date of Patent: Aug. 25, 1998

[54] PHYSICAL-INFORMATION-IMAGE DISPLAYING APPARATUS

[75] Inventor: Tohru Oka, Ichinomiya, Japan

[73] Assignee: Colin Corporation, Komaki, Japan

[21] Appl. No.: 710,144

[22] Filed: Sep. 13, 1996

[51] Int. Cl.$^6$ .................................................. G06F 15/68
[52] U.S. Cl. ........................... 600/300; 600/325; 600/341; 600/342; 600/486; 600/500; 600/101
[58] Field of Search ............................ 128/633, 644–7; 600/101, 103, 109, 113, 310, 322, 323, 342, 341, 485, 486, 500; 349/5–7

[56] References Cited

U.S. PATENT DOCUMENTS

| | | | |
|---|---|---|---|
| 4,950,072 | 8/1990 | Honda | 349/6 |
| 4,995,396 | 2/1991 | Inaba et al. | |
| 5,041,965 | 8/1991 | Chen | |
| 5,140,519 | 8/1992 | Friesdorf et al. | 128/709 |
| 5,351,677 | 10/1994 | Kami et al. | |
| 5,404,185 | 4/1995 | Vogeleg et al. | 349/6 |
| 5,408,998 | 4/1995 | Mersch | 128/633 |

FOREIGN PATENT DOCUMENTS

| | | |
|---|---|---|
| 0566861 | 10/1993 | European Pat. Off. |
| 0569670 | 11/1993 | European Pat. Off. |
| 0665686 | 2/1995 | European Pat. Off. |
| 02104329 | 7/1990 | Japan |

Primary Examiner—Jennifer Bahr
Assistant Examiner—Bryan K. Yarnell
Attorney, Agent, or Firm—Oliff & Berridge, PLC

[57] ABSTRACT

A physical-information-image displaying apparatus for use with an endoscope including an image pick-up which picks up an endoscopic image from a living subject and produces an endoscopic-image signal representing the picked-up endoscopic image, and a display which displays the picked-up endoscopic image represented by the endoscopic-image signal, the apparatus including a physical-information obtaining device which obtains a physical information from the subject and produces a physical-information signal representing the obtained physical information, a physical-information-image-signal producing device which produces, based on the physical-information signal produced by the physical-information obtaining device, a physical-information-image signal representing a physical-information image corresponding to the obtained physical information, and a superimposing device which superimposes the physical-information-image signal produced by the physical-information-image-signal producing device, on the endoscopic-image signal produced by the image pick-up of the endoscope, so that the physical-information image represented by the physical-information-image signal is superimposed on the picked-up endoscopic image represented by the endoscopic-image signal, on the display of the endoscope.

29 Claims, 4 Drawing Sheets

PHYSICAL-INFORMATION-IMAGE DISPLAYING APPARATUS

BACKGROUND OF THE INVENTION

1. Field of the Invention

The present invention relates to a physical-information-image displaying apparatus for use with an endoscope including an image pick-up which picks up an endoscopic image from a living subject and produces an endoscopic-image signal representing the picked-up endoscopic image, and a display which displays the picked-up endoscopic image represented by the endoscopic-image signal.

2. Related Art Statement

There is known an endoscope including an image pick-up which picks up an endoscopic image from a living subject and produces an endoscopic-image signal representing the picked-up endoscopic image, and a display which displays the picked-up endoscopic image represented by the endoscopic-image signal. The endoscope is inserted, for, e.g., making a diagnosis or effecting a surgical operation, into, e.g., the stomach, intestine or other digestive tracts, or into the bladder, bronchial tubes, or abdominal cavity, of the subject, and takes an endoscopic image from the subject.

In order to monitor the physical condition of the subject on which the endoscope is being used, a blood pressure (BP) measuring device, a blood-oxygen-saturation measuring device, and/or a heart-rate measuring device may be used to measure periodically a BP value, a blood oxygen saturation value, and/or a heart rate value of the subject. However, the operator who is operating the endoscope is concentrating his or her attention on the endoscopic image being displayed on the screen of the display and accordingly cannot pay sufficient attention to the physical information, i.e., BP values, blood oxygen saturation values, and/or heart rate values obtained from the subject. Thus, the operator may fail to recognize a sudden change of the physical condition of the subject.

SUMMARY OF THE INVENTION

It is therefore an object of the present invention to provide a physical-information-image displaying apparatus which is for use with an endoscope and which enables an operator to recognize a sudden change of the physical condition of a living subject on whom the endoscope is being used.

The above object has been achieved by the present invention. According to a first aspect of the present invention, there is provided a physical-information-image displaying apparatus for use with an endoscope including an image pick-up which picks up an endoscopic image from a living subject and produces an endoscopic-image signal representing the picked-up endoscopic image, and a display which displays the picked-up endoscopic image represented by the endoscopic-image signal, the apparatus comprising a physical-information obtaining device which obtains a physical information from the subject and produces a physical-information signal representing the obtained physical information, a physical-information-image-signal producing device which produces, based on the physical-information signal produced by the physical-information obtaining device, a physical-information-image signal representing a physical-information image corresponding to the obtained physical information, and a superimposing device which superimposes the physical-information-image signal produced by the physical-information-image-signal producing device, on the endoscopic-image signal produced by the image pick-up of the endoscope, so that the physical-information image represented by the physical-information-image signal is superimposed on the picked-up endoscopic image represented by the endoscopic-image signal, on the display of the endoscope.

In the physical-information-image displaying apparatus in accordance with the first aspect of the invention, the physical-information image is superimposed on the endoscopic image on the display of the endoscope. The superimposing of the physical-information image encompasses both the manner in which the physical-information image overlaps an area or portion of the endoscopic image and the manner in which the physical-information image positions adjacent to the endoscopic image. Thus, the operator who is concentrating his or her attention to the endoscopic image being displayed on the display, can easily view the physical-information image together with the endoscopic image. Therefore, the operator can easily recognize a sudden change of the physical condition of the subject and take an appropriate action or treatment on the subject.

According to a preferred feature of the first aspect of the invention, the image displaying apparatus further comprises a control device which controls the superimposing device to cyclically superimpose the physical-information-image signal on the endoscopic-image signal, at a predetermined interval of time.

According to another feature of the first aspect of the invention, the control device comprises means for controlling the superimposing device to superimpose, in each cycle, the physical-information-image signal on the endoscopic image signal, for a duration equal to a predetermined proportion of the interval. In this case, the durations in each of which no physical-information image is superimposed on the endoscopic image are iteratively provided, so that the operator can observe the clear endoscopic images.

According to another feature of the first aspect of the invention, the image displaying apparatus further comprises judging means for judging whether the obtained physical information represented by the physical-information signal is abnormal.

According to another feature of the first aspect of the invention, the judging means comprises means for making a positive judgment that the obtained physical information is abnormal, when a measurement value as the obtained physical information does not fall within a predetermined normal range.

According to another feature of the first aspect of the invention, the physical-information-image-signal producing device comprises abnormality informing means for producing, as the physical-information-image signal, a first physical-information-image signal, when the judging means makes a negative judgment, and producing, as the physical-information-image signal, a second physical-information-image signal, when the judging means makes a positive judgment, and wherein the second physical-information-image signal represents the physical-information image in a manner different from a manner in which the first physical-information-image signal represents the physical-information image. In this case, the operator is visually informed of an abnormality of physical information obtained from the subject, so that the subject may not feel anxiety about the physical information.

According to another feature of the first aspect of the invention, the abnormality informing means comprises means for producing each of the first and second physical-information image signals such that the second physical-information image signal represents the physical-information image in bigger characters than those in which the first physical-information-image signal represents the physical-information image.

According to another feature of the first aspect of the invention, the abnormality informing means comprises means for producing each of the first and second physical-information image signals such that the second physical-information image signal represents the physical-information image in a different color from that in which the first physical-information-image signal represents the physical-information image.

According to another feature of the first aspect of the invention, the abnormality informing means comprises means for producing each of the first and second physical-information image signals such that the second physical-information image signal commands that the physical-information image be flashed at a predetermined frequency whereas the first physical-information-image signal commands that the physical-information image be displayed continuously.

According to another feature of the first aspect of the invention, the physical-information-image-signal producing device comprises abnormality informing means for producing the physical-information image signal, when the judging means makes a positive judgment, and not producing the physical-information-image signal, when the judging means makes a negative judgment.

According to another feature of the first aspect of the invention, the physical-information obtaining device comprises at least one of a blood-pressure measuring device, a blood-oxygen-saturation measuring device, and a heart-rate measuring device.

According to a second aspect of the present invention, there is provided a physical-information-image displaying apparatus for use with an endoscope including an image pick-up which picks up an endoscopic image from a living subject and produces an endoscopic-image signal representing the picked-up endoscopic image, and an endoscopic-image display which displays the picked-up endoscopic image represented by the endoscopic-image signal, the apparatus comprising a physical-information obtaining device which obtains a physical information from the subject and produces a physical-information signal representing the obtained physical information, a physical-information-image-signal producing device which produces, based on the physical-information signal produced by the physical-information obtaining device, a physical-information-image signal representing a physical-information image corresponding to the obtained physical information, a liquid-crystal display which is provided on an image screen of the endoscopic-image display and which is transparent so that the image screen is visible through the liquid-crystal display, and a control device which controls the liquid-crystal display to display the physical-information image represented by the physical-information-image signal, so that the physical-information image is superimposed on the picked-up endoscopic image displayed on the endoscopic-image display.

In the physical-information-image displaying apparatus in accordance with the second aspect of the invention, the physical-information image which is displayed by the basically transparent liquid-crystal display provided on the screen of the endoscopic-image display, is superimposed on the endoscopic image which is displayed on the endoscopic-image display. The superimposing of the physical-information image encompasses both the manner in which the physical-information image overlaps an area or portion of the endoscopic image and the manner in which the physical-information image positions adjacent to the endoscopic image. Thus, the operator who is concentrating his or her attention to the endoscopic image being displayed on the endoscopic-image display, can easily view the physical-information image being displayed by the liquid-crystal display. Therefore, the operator can easily recognize a sudden change of the physical condition of the subject and take an appropriate action or treatment on the subject.

According to a preferred feature of the second aspect of the invention, the liquid-crystal display comprises a matrix of picture elements and means for applying light to picture elements of a portion of the matrix which correspond to at least one character as the physical-information image, so that the picture elements of the portion are made translucent.

According to another feature of the second aspect of the invention, the control device comprises means for controlling the liquid-crystal display to cyclically display the physical-information image, at a predetermined interval of time.

According to another feature of the second aspect of the invention, the control device further comprises means for controlling the liquid-crystal display to display, in each cycle, the physical-information image, for a duration equal to a predetermined proportion of the interval.

According to another feature of the second aspect of the invention, the image displaying apparatus further comprises judging means for judging whether the obtained physical information represented by the physical-information signal is abnormal.

According to another feature of the second aspect of the invention, the judging means comprises means for making a positive judgment that the obtained physical information is abnormal, when a measurement value as the obtained physical information does not fall within a predetermined normal range.

According to another feature of the second aspect of the invention, the physical-information-image-signal producing device comprises abnormality informing means for producing, as the physical-information-image signal, a first physical-information-image signal, when the judging means makes a negative judgment, and producing, as the physical-information-image signal, a second physical-information-image signal, when the judging means makes a positive judgment, and wherein the second physical-information-image signal represents the physical-information image in a manner different from a manner in which the first physical-information-image signal represents the physical-information image.

According to another feature of the second aspect of the invention, the physical-information-image-signal producing device comprises abnormality informing means for producing the physical-information image signal, when the judging means makes a positive judgment, and not producing the physical-information-image signal, when the judging means makes a negative judgment.

According to another feature of the second aspect of the invention, the physical-information obtaining device comprises at least one of a blood-pressure measuring device, a blood-oxygen-saturation measuring device, and a heart-rate measuring device.

BRIEF DESCRIPTION OF THE DRAWINGS

The above and optional objects, features, and advantages of the present invention will better be understood by reading the following detailed description of the preferred embodiments of the invention when considered in conjunction with the accompanying drawings, in which.

DETAILED DESCRIPTION OF THE PREFERRED EMBODIMENTS

Figure 1:
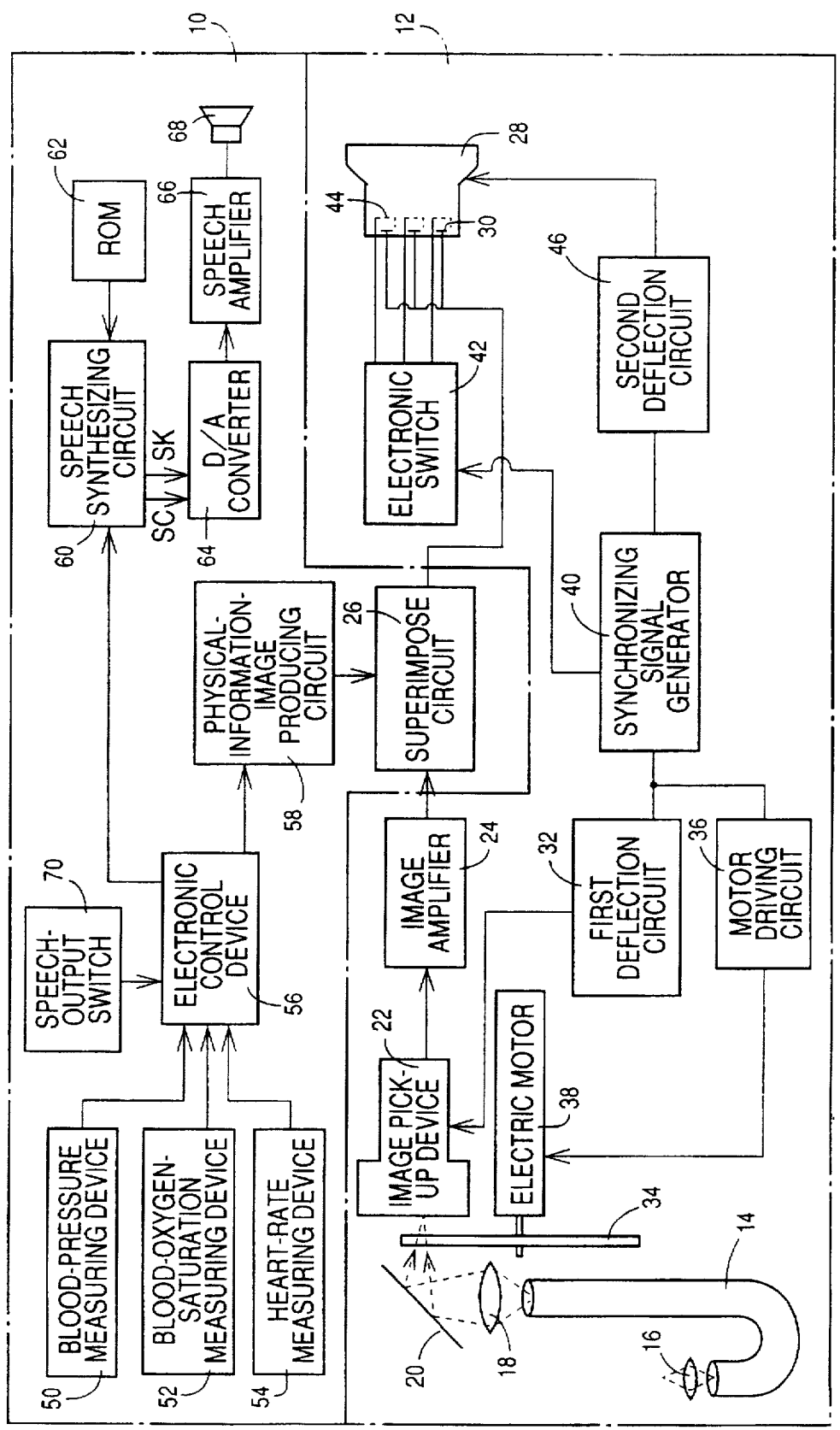
FIG. 1 is a diagrammatic view of an endoscope system including an endoscope apparatus, and a physical-information displaying apparatus to which the present invention is applied; .
Figure 2:
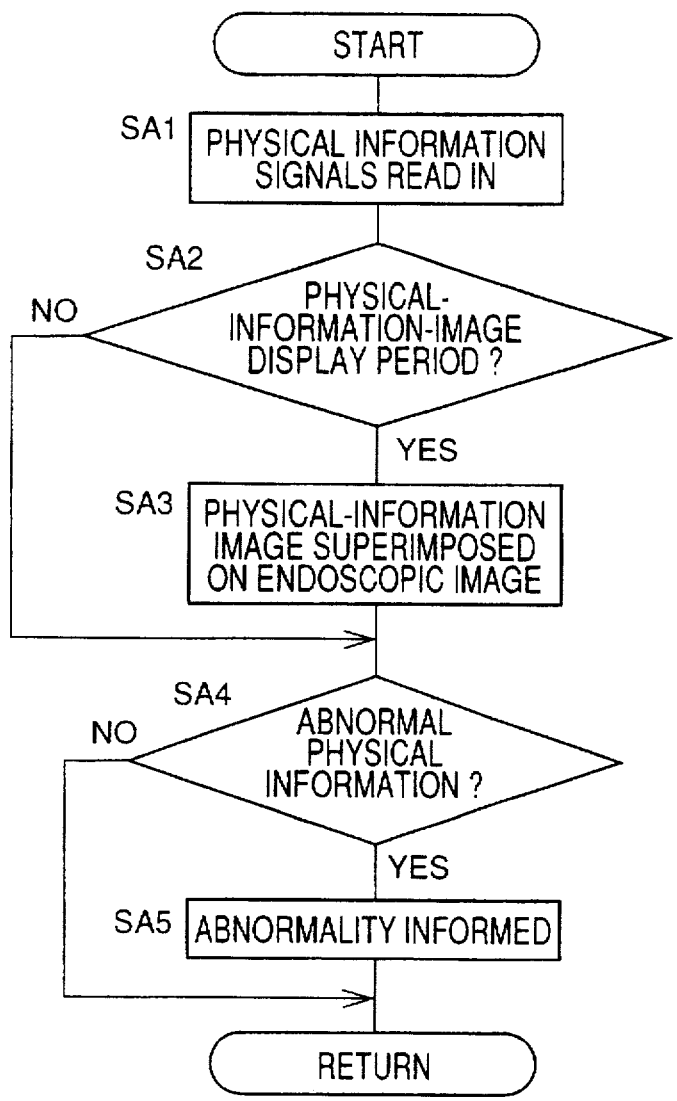
FIG. 2 is a flow chart representing a control program according to which the displaying apparatus of FIG. 1 is operated.
Figure 3:
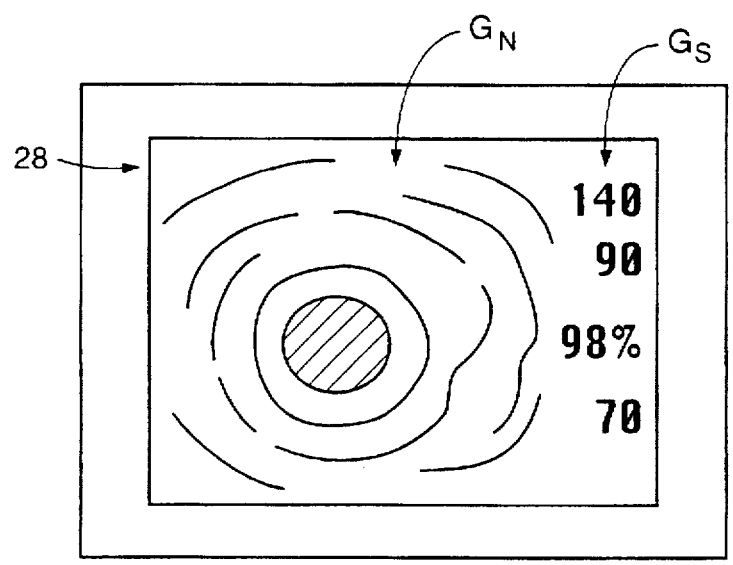
FIG. 3 is a view of an endoscopic image and a physical-information image superimposed on the endoscopic image which are displayed by a color cathode ray tube (CRT) as an endoscopic-image display of the endoscope apparatus of FIG. 1.

Referring first to FIGS. 1 through 3, there will be described an endoscope system including an endoscope apparatus 12, and a physical-information-image displaying apparatus 10 to which the present invention is applied.

As shown in FIG. 1, the endoscope apparatus 12 includes an optical-fiber device 14 including a light guide which transmits an irradiating light generated from a light source (not shown), and an image fiber which transmits an endoscopic image of, e.g., the inner wall of stomach of a patient irradiated by the light. The optical fiber 14 is provided by a bundle of glass fibers each of which has a diameter of several microns, and accordingly has a high flexibility. Thus, the optical fiber 14 can reach an internal, deep portion of the patient via a meandering path such as mouth and esophagus.

The optical fiber 14 transmits the endoscopic image formed on one end face thereof by an object lens 16, to the other end face thereof, so that the endoscopic image is formed on an image pick-up device 22 via an image-forming lens 18 and a reflecting mirror 20. The image pick-up 22 is provided by, e.g., an image orthicon or a CCD (charge-coupled devices) image sensor. The image pick-up 22 produces an endoscopic-image signal representing the endoscopic image obtained by the optical fiber 14, and supplies the endoscopic-image signal to three cathodes (electron guns) 30 of a color cathode ray tube (CRT) 28 via an image-signal amplifier 24 and a superimpose circuit 26. The color CRT 28 provides an endoscopic-image display of the endoscope apparatus 12. The image pick-up 22 outputs, in response to a timing signal supplied from a first deflection circuit 32, scanning-line signals respectively corresponding to scanning lines of the color CRT 28. A three-color filter 34 is provided between the image-forming lens 18 and the image pick-up 22, and is driven or rotated by an electric motor 38 under control of a motor driving circuit 36. Thus, the endoscopic image obtained by the optical fiber 14 is separated into the three primary colors, i.e., red, green, and blue, and each of the frames provided by the endoscopic-image signal output from the image pick-up 22 has one of the three primary colors.

In response to the timing signal supplied from the first deflection circuit 32, a synchronizing signal generator 40 supplies a synchronizing signal to an electronic switch 42 which switches, in response to the synchronizing signal, three control grids 44 of the color CRT 28, from one to another. Thus, the respective electron beams emitted from the three cathodes 30 are switched from one to another, and the red, green, and blue frames provided by the endoscopic-image signal are displayed in turn on the screen of the color CRT 28. Thus, the endoscopic image is seen as a full-color image by an operator. In response to the timing signal from the first deflection circuit 32, a second deflection circuit 46 supplies a deflection signal to a deflection coil of the color CRT 28 to deflect the electron beams emitted from the cathodes 30.

The physical-information-image displaying apparatus 10 includes a blood-pressure (BP) measuring device 50 which measures a BP value, BP, (mmHg) of the patient on whom the endoscope apparatus 50 is being used; a blood-oxygen-saturation measuring device (i.e., pulse oximeter) 52 which optically measures a blood oxygen saturation, OX, (%) of the patient; and a heart-rate measuring device 54 which measures a heart rate, HR, (/min) of the patient. Each of the three measuring devices 50, 52, 54 produces a physical-information signal (i.e., electric signal) representing the detected physical information, and supplies the signal to an electronic control device 56. In the present embodiment, each of the three measuring devices 50, 52, 54 provides a physical-information obtaining device.

The electronic control device 56 is provided by a microcomputer including a central processing unit (CPU, not shown), a read only memory (ROM, not shown), and a random access memory (RAM, not shown). The CPU processes each of the respective physical-information signals supplied from the three measuring devices 50, 52, 54, according to control programs pre-stored in the ROM, by utilizing a temporary-storage function of the RAM, and supplies data indicative of a value as each of the three sorts of physical information, and/or data indicative of an abnormality of each physical information, to each of a physical-information-image-signal producing circuit 58, a speech-signal synthesizing circuit 60, and a portable vibration producing device 61.

The physical-information-image-signal producing circuit 58 produces a physical-information-image signal representing a physical information image including a value (i.e., digits) as each of the respective sorts of physical information obtained by the three measuring devices 50, 52, 54, i.e., BP value BP (mmHg), oxygen saturation OX (%), and heart rate HR (/min). The physical-information-image signal indicates that the physical-information image be displayed in a predetermined area on the screen of the color CRT 28. The superimpose circuit 26 superimposes the physical-information-image signal on the endoscopic-image signal supplied from the image-signal amplifier 24 to the CRT 28, so that the physical-information image is superimposed on the endoscopic image on the screen of the CRT 28. The superimpose circuit 26 is provided by a commercially available superimpose IC (integrated circuit) which is well known in the art and is commonly used for superimposing a number indicative of a current channel and/or a number indicative of a current day time, on a screen image of a CRT.

The abnormality informing apparatus 10 further includes a speech-signal storing ROM 62 which stores, in advance, a plurality of code signals, SC, representing a plurality of sorts of speech, respectively. For example, a code signal SCBP corresponding to blood pressure represents a speech or voice that the systolic BP value of the patient is 140 mmHg and the diastolic BP value is 90 mmHg; a code signal $SC_{OX}$ corresponding to blood oxygen saturation represents a speech that the blood oxygen saturation of the patient is 98%; and a code signal $SC_{HR}$ corresponding to heart rate represents a speech that the heart rate of the patient is 70 per minute. A speech-output switch 70 is manually operable by the operator for selectively placing the abnormality informing apparatus 10 in a speech-output mode in which the apparatus 10 outputs a speech and a silent mode in which the apparatus 10 does not output any speech. With the speech-output switch 70 being switched to the speech-output mode, the speech-signal synthesizing circuit 60 selects one of the code signals which corresponds to a command signal supplied from the control device 56 with respect to each of the obtained three sorts of physical information. The thus selected three code signals $SC_{BP}$, $SC_{OX}$, $SC_{HR}$ are supplied to a digital-to-analog (D/A) converter 64. In addition, the speech-signal synthesizing circuit 60 selects one of a plurality of clock signals, SK, representing different clock frequencies, according to a command signal supplied from the control device 56 with respect to each of the obtained three sorts of physical information. The thus selected three clock signals $SK_{BP}$, $SK_{OX}$, $SK_{HR}$ are supplied to the D/A converter 64.

The D/A converter 64 converts each code signal SC ($SK_{BP}$, $SC_{OX}$, $SC_{HR}$) into an analog speech signal having a waveform representing a speech corresponding to the obtained physical information BP, OX, HR, at the frequency or period represented by a corresponding clock signal SK ($SK_{BP}$, $SK_{OX}$, $SK_{HR}$). Thus, the speech represented by each speech signal has frequencies in a predetermined range corresponding to the frequency represented by a corresponding clock signal SK. Each speech signal is amplified by a speech-signal amplifier 66 and then is supplied to a speaker 68 as a speech outputting device, so that the speaker 68 outputs the speech represented by the speech signal. Thus, the speech-signal synthesis is effected by a so-called pulse code modulation.

There will be described the operation of the abnormality informing apparatus 10 constructed as described above, by reference to the flow chart of FIG. 2 which represents a control program pre-stored in the ROM of the control device 56. First, at Step SA1, the CPU of the control device 56 reads in the respective physical-information signals supplied from the three measuring devices 50, 52, 54. Step SA1 is followed by Step SA2 to judge whether it is now within a cyclic physical-information-image displaying duration. The cycle time of each duration is, e.g., 15 seconds, and each duration lasts one third to one fifth of the cycle time.

If a negative judgment is made at Step SA2, the control of the CPU goes to Step SA4. On the other hand, if a positive judgment is made at Step SA2, the control of the CPU goes to Step SA3 to supplies data indicative of a value as each of the respective sorts of physical information obtained by the three measuring devices 50, 52, 54, i.e., BP value BP (mmHg), oxygen saturation OX (%), and heart rate HR (/min), to the physical-information-image-signal producing circuit 58, which produces a physical-information-image signal representing a physical-information image including the value as each of the three sorts of physical information. The superimpose circuit 26 superimposes the physical-information-image signal representing the physical-information image, on the endoscopic-image signal representing the endoscopic image, so that the physical-information image, $G_S$, is superimposed on a right-hand end area of the endoscopic image, $G_N$, on the screen of the color CRT 28, as shown in FIG. 3. In FIG. 3, values "140" and "90" shown in the top of the image $G_S$ represent a systolic and a diastolic BP value $BP_{SYS}$, $BP_{DIA}$ of the patient, respectively; value "98%" in the middle of the image $G_S$ represents a blood oxygen saturation OX of the patient; and value "70" in the bottom of the image $G_S$ represents a heart rate HR of the patient. At Step SA3, the physical-information values $BP_{SYS}$, $BP_{DIA}$, OX, HR are displayed in small characters and in white color.

In addition, at Step SA3, if the speech-output switch 70 is set at the speech-output mode, the CPU of the control device 56 supplies, only one time, the data indicative of the value as each of the respective sorts of physical information BP, OX, HR, to the speech-signal synthesizing circuit 60, so that finally the speaker 68 outputs a speech or voice corresponding to each of the three sorts of physical information BP, OX, HR. At Step SA3, the synthesizing circuit 60 supplies, to the D/A converter 64, a clock signal, $SK_{LF}$, indicative of the lower one of two different frequencies, with respect to each of the three sorts of physical information BP, OX, HR, i.e., three sorts of code signals $CS_{BP}$, $SC_{OX}$, $SC_{HR}$, so that the speaker 68 outputs each speech in a low voice like a man. Step SA3 is followed by Step SA4.

At Step SA4, the CPU of the control device 56 judges whether each of the systolic and diastolic BP values, blood oxygen saturation OX, and heart rate HR of the patient read in at Step SA1 is abnormal. This judgment is made by judging whether a value as each physical information falls within a corresponding predetermined normal range. A negative judgment is made at Step SA4 if the value as each physical information falls within the corresponding predetermined normal range. In this case, the present routine is ended. On the other hand, a positive judgment is made at Step SA4 if the value as each physical information does not fall within the corresponding predetermined normal range. In the latter case, the control of the CPU goes to Step SA5. Thus, Step SA4 corresponds to abnormality judging means.

At Step SA5, the CPU of the control device 56 controls the physical-information-image-signal producing circuit 58 to produce an abnormal-physical-information-image signal representing a physical-information image corresponding to an abnormal physical information, in a manner different from that in which a normal-physical-information-image signal represents a physical-information image corresponding to a normal physical information. For example, the abnormal physical information or value may be displayed in bigger characters, in a darker color such as black or blue, or in a warning color such as red, orange, or yellow, or may be flashed at a predetermined frequency.

In addition, at Step SA5, if the speech-output switch 70 is set at the speech-output mode, the CPU of the control device 56 supplies the data indicative of the value as each of the respective sorts of physical information BP, OX, HR, to the speech-signal synthesizing circuit 60, so that finally the speaker 68 outputs a speech or voice corresponding to each of the three sorts of physical information BP, OX, HR. At Step SA5, however, the CPU controls the synthesizing circuit 60 to supply, to the D/A converter 64, a clock signal, $SK_{HF}$, indicative of the higher one of the two different frequencies, with respect to each of the three sorts of physical information BP, OX, HR or the three sorts of code signals $CS_{BP}$, $SC_{OX}$, $SC_{HR}$, so that the speaker 68 outputs each speech in a loud voice like a woman.

As is apparent from the foregoing description, in the present embodiment, the BP measuring device 50, the blood-oxygen-saturation measuring device 52, and the heart-rate measuring device 54 measure, as physical information, a systolic and a diastolic BP value BP, a blood oxygen saturation OX, and a heart rate HR, of the patient, respectively, and the physical-information-image-signal producing circuit 58 produces a physical-information-image signal representing a physical-information image $G_S$ corresponding to the measured values BP, OX, HR. In addition, the superimpose circuit 26 superimposes the thus produced physical-information-image signal on the endoscopic-image signal supplied to the color CRT 28, so that the physical-information image $G_S$ is superimposed on the endoscopic image $G_N$ on the screen of the CRT 28. Thus, even an operator such as a doctor who is concentrating his or her attention on the endoscopic image $G_N$ being displayed on the CRT 28, can easily view the physical-information image $G_S$ together with the endoscopic image $G_N$ on the CRT 28. Accordingly, the operator can easily recognize a sudden change of the physical condition of the patient who is undergoing the endoscopy.

Also, in the present embodiment, at Step SA2, the physical-information image $G_S$ is cyclically displayed together with the endoscopic image $G_N$ on the CRT 28, at a predetermined regular interval of time, each for a duration equal to a predetermined proportion of the interval time. Thus, the durations in each of which no physical-information image $G_S$ is displayed are cyclically provided, and the operator can easily observe the endoscopic image $G_N$ displayed on the CRT 28.

In addition, in the present embodiment, at Step SA4, the control device 56 judges whether each of the physical-information values BP, OX, HR is abnormal. If at Step SA4 a positive judgment is made with respect to at least one of the three sorts of physical information BP, OX, HR, the control device 56 controls, at Step SA5, the physical-information-image-signal producing circuit 58 to produce an abnormal-physical-information-image signal which represents the abnormal physical-information image in a different manner from that in which a normal-physical-information-image signal represents a normal physical-information image. For example, the abnormal physical-information image $G_S$ is displayed, on the color CRT 28, in a different color (e.g., black, blue, red, orange, or yellow) from the color (e.g., white or green) in which the normal physical-information image $G_S$ is displayed. Thus, the operator who is concentrating his or her attention on the endoscopic image $G_N$ being displayed on the CRT 28, can easily recognize the abnormality of the physical information obtained from the patient.

Figure 4:
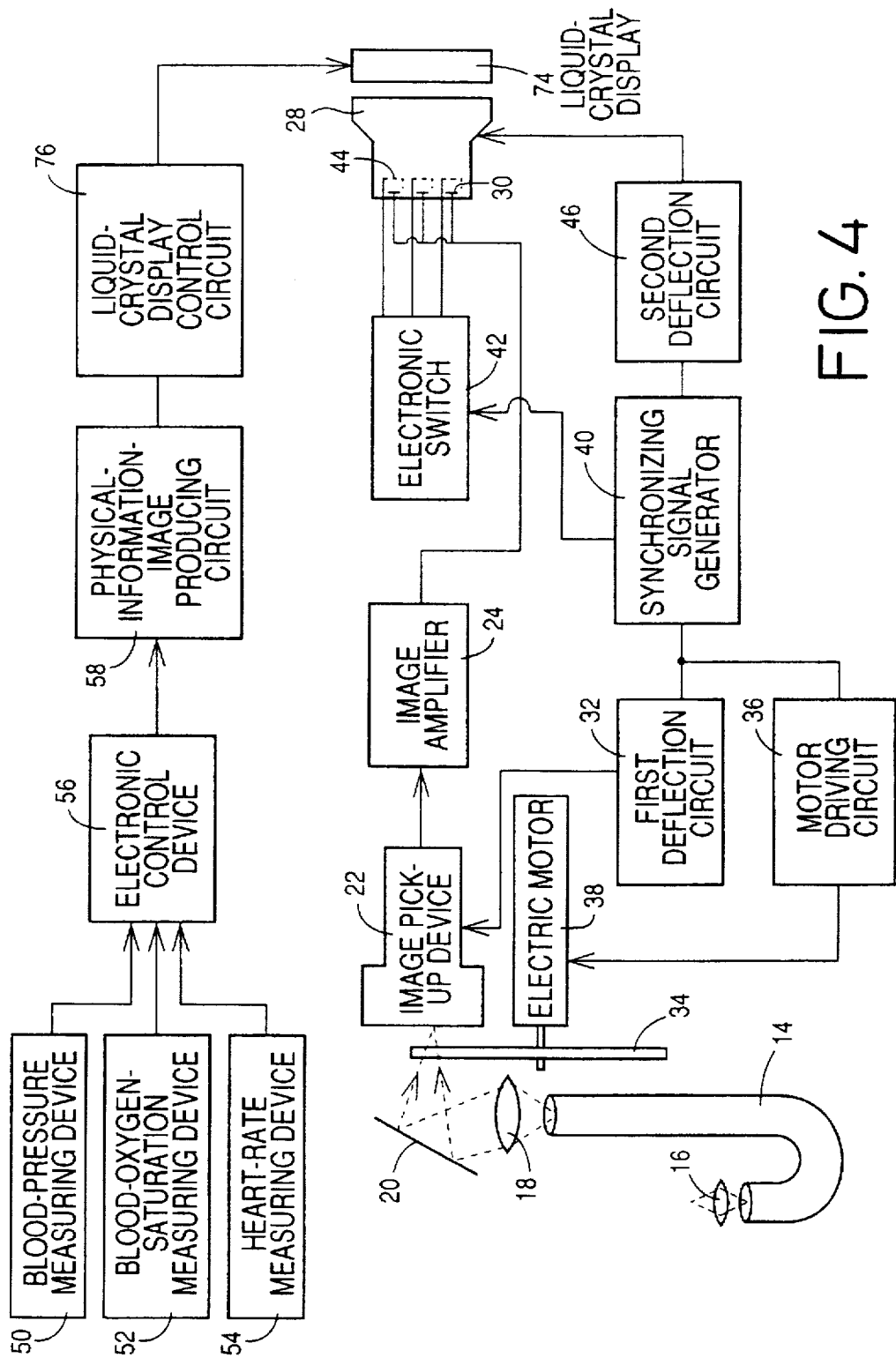
FIG. 4 is a view corresponding to FIG. 1, showing another endoscope system as a second embodiment of the present invention.

Referring next to FIG. 4, there will be described a second embodiment of the present invention. The second embodiment also relates to an endoscope system including an endoscope apparatus including an image pick-up device 22 and a color CRT 28, and a physical-information-image displaying apparatus including a physical-information obtaining device 50, 52, 54 and a physical-information-image-signal producing circuit 58. The second embodiment has basically the same hardware construction as that of the first embodiment shown in FIG. 1, and is operated according to the same software as that shown in FIG. 2. The same reference numerals as used in the first embodiment shown in FIGS. 1 to 3 are used to designate the corresponding elements or parts of the second embodiment shown in FIG. 4, and the description of those elements or parts is omitted. The following description relates to only the differences of the second embodiment from the first embodiment.

In the second embodiment shown in FIG. 4, a liquid-crystal display (LCD) 74 is provided on a screen of a color CRT 28. The LCD 74 includes a transparent nematic liquid-crystal plate so that an operator or observer can see an endoscopic image $G_N$ being displayed on the screen of the CRT 28 through the transparent plate of the LCD 74. The liquid-crystal plate provides a matrix of picture elements which cooperate with one another to display a white-color character or characters (numerals, alphabets, and/or symbols) because of scattering of the light applied to appropriate ones of the picture elements. A liquid-crystal-display control circuit 76 drives the LCD 74 in an appropriate drive manner and with an appropriate drive voltage, so that a physical-information image $G_S$ represented by a physical-information-image signal produced by the physical-information-image-signal producing circuit 58 is displayed in a predetermined area of the LCD 74, as shown in FIG. 3. Thus, the physical-information image $G_S$ is superimposed on the endoscopic image $G_N$ displayed on the CRT 28.

In the second embodiment, the BP measuring device 50, the blood-oxygen-saturation measuring device 52, and the heart-rate measuring device 54 measure, as physical information, a systolic and a diastolic BP value BP, a blood oxygen saturation OX, and a heart rate HR, of the patient, respectively, and the physical-information-image-signal producing circuit 58 produces a physical-information-image signal representing a physical-information image $G_S$ corresponding to the measured values BP, OX, HR. In addition, the LCD control circuit 76 controls the LCD 74 to display the physical-information image $G_S$ represented by the physical-information-image signal, so that the physical-information image $G_S$ is superimposed on the endoscopic image $G_N$ being displayed on the color CRT 28. Thus, even an operator such as a doctor who is concentrating his or her attention on the endoscopic image $G_N$ displayed on the CRT 28, can easily view the physical-information image $G_S$ together with the endoscopic image $G_N$. Accordingly, the operator can easily recognize a sudden change of the physical condition of the patient who is undergoing the endoscopy.

While the present invention has been described in its preferred embodiments, the present invention may otherwise be embodied.

For example, while in each of the illustrated embodiments the physical-information image $G_S$ overlaps a predetermined area or portion of the endoscopic image $G_N$, it is possible to display the physical-information image $G_S$ at a position adjacent to the endoscopic image $G_N$. As far as the present invention is concerned, the term "superimposing" is defined as encompassing both the cases.

Although in each of the illustrated embodiments the color CRT 28 is employed to display the full-color endoscopic image $G_N$, it is possible to employ a black-and-white CRT which displays a monochromatic endoscopic image.

While in each of the illustrated embodiments the single image pick-up device 22 and the three-color filter 34 are employed to produce, by time sharing, respective image signals corresponding to the three primary colors and thereby provide the full-color endoscopic image $G_N$, it is possible to employ three image pick-up devices corresponding to the three primary colors, so that the three image pick-up devices concurrently produces respective image signals corresponding to the three primary colors and thereby provide a full-color endoscopic image $G_N$.

Although in each of the illustrated embodiments the three physical-information obtaining devices, i.e., BP measuring device 50, oxygen-saturation measuring device 52, and heart-rate measuring device 54 are employed, it is possible to employ only one or two of the three devices 50, 52, 54, or employ one or more other devices for measuring one or more other sorts of physical information, such as respiration rate or arrhythmia.

In each of the illustrated embodiments, Step SA2 and SA3 of FIG. 2 may be omitted. In the latter case, the physical-information image $G_S$ is superimposed on the endoscopic image $G_N$ only when an abnormality of the physical information is identified at Step SA4. Thus, the operator can concentrate his or her attention on the endoscopic image $G_N$ being displayed on the CRT 28. In the latter case, the abnormal physical-information image $G_S$ (BP, OX, and/or HR) may be displayed in the same manner as the above-described manner employed at Step SA3.

Although in each of the illustrated embodiments the displaying of the physical-information image $G_S$ lasts only a predetermined duration in each image displaying cycle, it is possible to display the image $G_S$ for a predetermined duration of about several seconds immediately after each physical-information obtaining device 50, 52, 54 detects or reads a value of a corresponding sort of physical information.

It is to be understood that the present invention may be embodied with other changes, improvements, and modifications that may occur to those skilled in the art without departing from the scope and spirit of the invention defined in the appended claims.

What is claimed is:

1. A physical-information-image displaying apparatus for use with an endoscope including an image pick-up which picks up an endoscopic image from a living subject and produces an endoscopic-image signal representing the picked-up endoscopic image, and a display screen, the display screen displays the picked-up endoscopic image represented by the endoscopic-image signal, the apparatus comprising:

a physical-information obtaining device which obtains physical information from the subject and produces a physical-information signal representing the obtained physical information, said physical-information obtaining device comprising at least one of a blood-pressure measuring device, a blood-oxygen-saturation measuring device, and a heart-rate measuring device;

a physical-information-image-signal producing device which produces, based on said physical-information signal produced by said physical-information obtaining device, a physical-information-image signal representing a physical-information image corresponding to said obtained physical information; and a superimposing device which superimposes said physical-information-image signal on the endoscopic-image signal so that said physical-information is displayed on a predetermined portion of the display screen while being superimposed on a corresponding portion of the picked-up endoscopic image on the predetermined portion of the display screen, the physical-information image and a remaining portion of the picked-up endoscopic image are simultaneously displayed on the display screen.

2. An apparatus according to claim 1, further comprising a control device which controls said superimposing device to cyclically superimpose said physical-information-image signal on the endoscopic-image signal, at a predetermined interval of time.

3. An apparatus according to claim 2, wherein said control device comprises means for controlling said superimposing device to superimpose, in each cycle, said physical-information-image signal on the endoscopic image signal, for a duration equal to a predetermined portion of said interval.

4. An apparatus according to claim 1, further comprising judging means for judging whether said obtained physical information represented by said physical-information signal is abnormal.

5. An apparatus according to claim 4, wherein said judging means comprises means for making a positive judgment that said obtained physical information is abnormal, when a measurement value as said obtained physical information does not fall within a predetermined normal range.

6. An apparatus according to claim 4, wherein said physical-information-image-signal producing device comprises abnormality informing means for producing, as said physical-information-image signal, a first physical-information-image signal, when said judging means makes a negative judgment, and producing, as said physical-information-image signal, a second physical-information-image signal, when said judging means makes a positive judgment, and wherein said second physical-information-image signal represents said physical-information image in a manner different from a manner in which said first physical-information-image signal represents the physical-information image.

7. An apparatus according to claim 6, wherein said abnormality informing means comprises means for producing each of said first and second physical-information image signals such that the second physical-information image signal represents said physical-information image in bigger characters than those in which the first physical-information-image signal represents the physical-information image.

8. An apparatus according to claim 6, wherein said abnormality informing means comprises means for producing each of said first and second physical-information image signals such that the second physical-information image signal represents said physical-information image in a different color from that in which the first physical-information-image signal represents the physical-information image.

9. An apparatus according to claim 6, wherein said abnormality informing means comprises means for producing each of said first and second physical-information image signals such that the second physical-information image signal commands that said physical-information image be flashed at a predetermined frequency whereas the first physical-information-image signal commands that the physical-information image be displayed continuously.

10. An apparatus according to claim 4, wherein said physical-information-image-signal producing device comprises abnormality informing means for producing said physical-information image signal, when said judging means makes a positive judgment, and not producing said physical-information-image signal, when said judging means makes a negative judgment.

11. An apparatus according to claim 1, wherein said predetermined portion of the display screen comprises a predetermined end portion of the display screen.

12. An apparatus according to claim 1, wherein said predetermined portion of the display screen is smaller than half an area of the display screen.

13. An apparatus according to claim 1, wherein said predetermined portion of the display screen is smaller than one-fourth an area of the display screen.

14. A physical-information-image displaying apparatus for use with an endoscope including an image pick-up which picks up an endoscopic image from a living subject and produces an endoscopic-image signal representing the picked-up endoscopic image, and an endoscopic-image display which displays the picked-up endoscopic image represented by the endoscopic-image signal, the apparatus comprising:

a physical-information obtaining device which obtains physical information from the subject and produces a physical-information signal representing the obtained physical information;

a physical-information-image-signal producing device which produces, based on said physical-information signal produced by said physical-information obtaining device, a physical-information-image signal representing a physical-information image corresponding to said obtained physical information;

a liquid-crystal display which is provided on an image screen of the endoscopic-image display and which is transparent so that said image screen is visible through said liquid-crystal display; and a control device which controls said liquid-crystal display to display said physical-information image represented by said physical-information-image signal, so that the physical-information image is superimposed on the picked-up endoscopic image displayed on the endoscopic-image display.

15. An apparatus according to claim 14, wherein said liquid-crystal display comprises a matrix of picture elements and means for applying light to picture elements of a portion of said matrix which correspond to at least one character as said physical-information image, so that said picture elements of said portion are made translucent.

16. An apparatus according to claim 14, wherein said control device comprises means for controlling said liquid-crystal display to cyclically display said physical-information image, at a predetermined interval of time.

17. An apparatus according to claim 16, wherein said control device further comprises means for controlling said liquid-crystal display to display, in each cycle, said physical-information image, for a duration equal to a predetermined portion of said interval.

18. An apparatus according to claim 14, further comprising judging means for judging whether said obtained physical information represented by said physical-information signal is abnormal.

19. An apparatus according to claim 18, wherein said judging means comprises means for making a positive judgment that said obtained physical information is abnormal, when a measurement value as said obtained physical information does not fall within a predetermined normal range.

20. An apparatus according to claim 18, wherein said physical-information-image-signal producing device comprises abnormality informing means for producing, as said physical-information-image signal, a first physical-information-image signal, when said judging means makes a negative judgment, and producing, as said physical-information-image signal, a second physical-information-image signal, when said judging means makes a positive judgment, and wherein said second physical-information-image signal represents said physical-information image in a manner different from a manner in which said first physical-information-image signal represents the physical-information image.

21. An apparatus according to claim 18, wherein said physical-information-image-signal producing device comprises abnormality informing means for producing said physical-information image signal, when said judging means makes a positive judgment, and not producing said physical-information-image signal, when said judging means makes a negative judgment.

22. An apparatus according to claim 14, wherein said physical-information obtaining device comprises at least one of a blood-pressure measuring device, a blood-oxygen-saturation measuring device, and a heart-rate measuring device.

23. A physical-information-image displaying apparatus for use with an endoscope including an image pick-up which picks up an endoscopic image from a living subject and produces an endoscopic-image signal representing the picked-up endoscopic image, and a display which displays the picked-up endoscopic image represented by the endoscopic-image signal, the apparatus comprising:

a physical-information obtaining device which obtains physical information from the subject and produces a physical-information signal representing the obtained physical information;

a physical-information-image-signal producing device which produces, based on said physical-information signal produced by said physical-information obtaining device, a physical-information-image signal representing a physical-information image corresponding to said obtained physical information;

a superimposing device which superimposes said physical-information-image signal on the endoscopic-image signal so that said physical-information image represented by the physical-information-image signal is superimposed on the picked-up endoscopic image represented by the endoscopic-image signal on the display; and judging means for judging whether said obtained physical information represented by said physical-information signal is abnormal, wherein said physical-information-image-signal producing device produces bigger physical-information image characters when said judging means makes a positive judgment than characters produced when said judging means makes a negative judgment.

24. A physical-information-image displaying apparatus for use with an endoscope including an image pick-up which picks up an endoscopic image from a living subject and produces an endoscopic-image signal representing the picked-up endoscopic image, and a display which displays the picked-up endoscopic image represented by the endoscopic-image signal, the apparatus comprising:

a physical-information obtaining device which obtains physical information from the subject and produces a physical-information signal representing the obtained physical information;

a physical-information-image-signal producing device which produces, based on said physical-information signal produced by said physical-information obtaining device, a physical-information-image signal representing a physical-information image corresponding to said obtained physical information;

a superimposing device which superimposes said physical-information-image signal on the endoscopic-image signal so that said physical-information image represented by the physical-information-image signal is superimposed on the picked-up endoscopic image represented by the endoscopic-image signal on the display; and judging means for judging whether said obtained physical information represented by said physical-information signal is abnormal, wherein said physical-information image is a different color when said judging means makes a positive judgment than a color when said judging means makes a negative judgment.

25. A physical-information-image displaying apparatus for use with an endoscope including an image pick-up which picks up an endoscopic image from a living subject and produces an endoscopic-image signal representing the picked-up endoscopic image, and a display which displays the picked-up endoscopic image represented by the endoscopic-image signal, the apparatus comprising:
- a physical-information obtaining device which obtains physical information from the subject and produces a physical-information signal representing the obtained physical information;
- a physical-information-image-signal producing device which produces, based on said physical-information signal produced by said physical-information obtaining device, a physical-information-image signal representing a physical-information image corresponding to said obtained physical information;
- a superimposing device which superimposes said physical-information-image signal on the endoscopic-image signal so that said physical-information image represented by the physical-information-image signal is superimposed on the picked-up endoscopic image represented by the endoscopic-image signal on the display; and
- judging means for judging whether said obtained physical information represented by said physical-information signal is abnormal.
- wherein when said physical-information image is represented by flashing characters at a predetermined frequency on the display when said judging means makes a positive judgment, and said physical-information image is represented by continuously displayed characters on the display when said judging means makes a negative judgment.

26. A physical-information-image displaying apparatus for use with an endoscope including an image pick-up which picks up an endoscopic image from a living subject and produces an endoscopic-image signal representing the picked-up endoscopic image, and a display which displays the picked-up endoscopic image represented by the endoscopic-image signal, the apparatus comprising:
- a physical-information obtaining device which obtains physical information from the subject and produces a physical-information signal representing the obtained physical information;
- a physical-information-image-signal producing device which produces, based on said physical-information signal produced by said physical-information obtaining device, a physical-information-image signal representing a physical-information image corresponding to said obtained physical information;
- a superimposing device which superimposes said physical-information-image signal on the endoscopic-image signal so that said physical-information image represented by the physical-information-image signal is superimposed on the picked-up endoscopic image represented by the endoscopic-image signal on the display; and
- judging means for judging whether said obtained physical information represented by said physical-information signal is abnormal,
- wherein said physical-information-image-signal producing device produces said physical-information-image signal when said judging means makes a positive judgment, and does not produce said physical-information-image signal when said judging means makes a negative judgment.

27. A physical-information-image displaying apparatus for use with an endoscope including an image pick-up which picks up an endoscopic image from a living subject and produces an endoscopic-image signal representing the picked-up endoscopic image, and a display screen, the display screen displays the picked-up endoscopic image represented by the endoscopic-image signal, the apparatus comprising:
- a physical-information obtaining device which obtains physical information from the subject and produces a physical-information signal representing the obtained physical information;
- a physical-information-image-signal producing device which produces, based on said physical-information signal produced by said physical-information obtaining device, a physical-information-image signal representing a physical-information image corresponding to said obtained physical information;
- a superimposing device which superimposes said physical-information-image signal produced by said physical-information-image-signal producing device, on the endoscopic-image signal produced by the image pick-up of the endoscope, so that said physical-information-image signal is displayed on a predetermined portion of the display screen while being superimposed on a corresponding portion of the picked-up endoscopic image on the predetermined portion of the display screen, the physical-information image and a remaining portion of the picked-up endoscopic image are simultaneously displayed on the display screen; and
- a control device which controls said superimposing device to cyclically superimpose the physical-information-image signal on the endoscopic-image signal, at a predetermined interval of time.

28. An apparatus according to claim 27, wherein said control device comprises means for controlling said superimposing device to superimpose, in each cycle, the physical-information-image signal on the endoscopic image signal, for a duration equal to a predetermined portion of said interval.

29. A physical-information-image displaying apparatus for use with an endoscope including an image pick-up which picks up an endoscopic image from a living subject and produces an endoscopic-image signal representing the picked-up endoscopic image, and a display screen, the display screen displays the picked-up endoscopic image represented by the endoscopic-image signal, the apparatus comprising:
- a physical-information obtaining device which obtains physical information from the subject and produces a physical-information signal representing the obtained physical information;
- a physical-information-image-signal producing device which produces, based on said physical-information signal produced by said physical-information obtaining device, a physical-information-image signal representing a physical-information image corresponding to said obtained physical-information;
- a superimposing device which superimposes said physical-information-image signal produced by said physical-information-image-signal producing device, on the endoscopic-image signal produced by the image pick-up of the endoscope, so that said physical-information image represented by the physical-information-image signal is displayed on a predetermined portion of the display screen while being superimposed on a corresponding portion of the picked-up endoscopic image on the predetermined portion of the display screen, the physical-information image and a remaining portion of the picked-up endoscopic image are simultaneously displayed on the display screen; and judging means for judging whether said obtained physical information represented by said physical-information signal is abnormal, said physical-information-image-signal producing device further comprising abnormality informing means for producing a first physical-information-image signal when said judging means makes a negative judgment and for producing a second physical-information-image signal when said judging means makes a positive judgment, said first physical-information-image signal represents said physical-information image in a manner different from a manner in which said second physical-information-image signal represents the physical-information image.

* * * * *